US00PP35289P2

(12) United States Plant Patent
Olesen

(10) Patent No.: US PP35,289 P2
(45) Date of Patent: Aug. 1, 2023

(54) HYBRID TEA ROSE PLANT NAMED 'POULREN038'

(50) Latin Name: *Rosa hybrida*
Varietal Denomination: Poulren038

(71) Applicant: Mogens Nyegaard Olesen, Fredensborg (DK)

(72) Inventor: Mogens Nyegaard Olesen, Fredensborg (DK)

(73) Assignee: POULSEN ROSER A/S, Fredensborg (DK)

( * ) Notice: Subject to any disclaimer, the term of this patent is extended or adjusted under 35 U.S.C. 154(b) by 0 days.

(21) Appl. No.: 17/803,622

(22) Filed: Sep. 13, 2022

(30) Foreign Application Priority Data

Sep. 24, 2021 (QZ) ..... PBR 2021/2355

(51) Int. Cl.
*A01H 5/02* (2018.01)
*A01H 6/74* (2018.01)

(52) U.S. Cl.
USPC ..... Plt./137

(58) Field of Classification Search
USPC ..... Plt./137, 107, 148
CPC ... A01H 5/02; A01H 5/00; A01H 6/74; A01H 6/749
See application file for complete search history.

(56) References Cited

PUBLICATIONS

Floraland Poulsen Roser A/S 2020 retrieved on Nov. 14, 2022 at http://flora-land.ro/floraland/wp-content/uploads/2020/10/Floraland-Trandafir-si-clematis.pdf, 18 pp. (Year: 2020).*
Poulsen Roser A/S Nelly, retrieved on Nov. 14, 2022 at https://www.poulsenroser.dk/en/Roses/ShowProduct/67889, 2 pp. (Year: 2022).*

* cited by examiner

*Primary Examiner* — June Hwu

(57) ABSTRACT

A new garden rose plant of the Hybrid Tea class which has abundant, pink flowers and attractive foliage. This new and distinct variety has shown to be uniform and stable in the resulting generations from asexual propagation.

3 Drawing Sheets

Botanical designation: *Rosa hybrida.*
Variety denomination: 'Poulren038'.

This application claims priority to Plant Breeder's Rights Application Number 2021/2355, which was filed at the Community Plant Variety Rights Office in the European Union on Sep. 24, 2021, the contents of which are hereby incorporated by reference for all purposes.

SUMMARY OF THE INVENTION

The present invention constitutes a new and distinct variety of rose plant which originated from a controlled crossing between the female seed parent, an unnamed. seedling, and the male pollen parent, also an unnamed seedling. Both of the parent varieties are non-patented.

The two parents were crossed during the summer of 2013 and the resulting seeds were planted in a controlled environment in Fredensborg, Denmark. The new variety, named 'Poulren038', originated as a single seedling from the stated cross.

The new variety may be distinguished from its male pollen parent and female seed parent primarily by the following characteristics. The male pollen parent plant has dark pink flowers while the new variety has medium pink flowers. The female seed parent plant has white pink flowers while the new variety has pink flowers.

The objective of the hybridization of this rose variety was to create a new and distinct variety with unique qualities, such as:

1. Uniform and abundant pink flowers with very strong perfume;
2. Vigorous, but compact growth when propagated on its own roots;
3. Exceptional disease resistance.

This combination of qualities is not present in previously available commercial cultivars of this type, known to the inventor, and distinguish 'Poulren038' from all other varieties of which we are aware.

As part of the rose development program, Mogens N. Olesen germinated the seeds from the aforementioned hybridization during winter of 2013 and conducted evaluations on the resulting seedlings in a controlled environment in Fredensborg, Denmark. 'Poulren038' was selected in the spring of 2014 by the inventor as a single plant from the progeny of the aforementioned hybridization.

Asexual reproduction of 'Poulren038' by rooted cuttings was first done by Mogens N. Olesen in the nursery in Fredensborg, Denmark in July, 2014. This initial and other subsequent asexual propagations conducted in controlled environments have demonstrated that the characteristics of 'Poulren038' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulren038'.

Specifically illustrated in FIG. 1 of the drawings are open flowers viewed from above and the side, as well as a cluster of flower buds.

Figure 1:
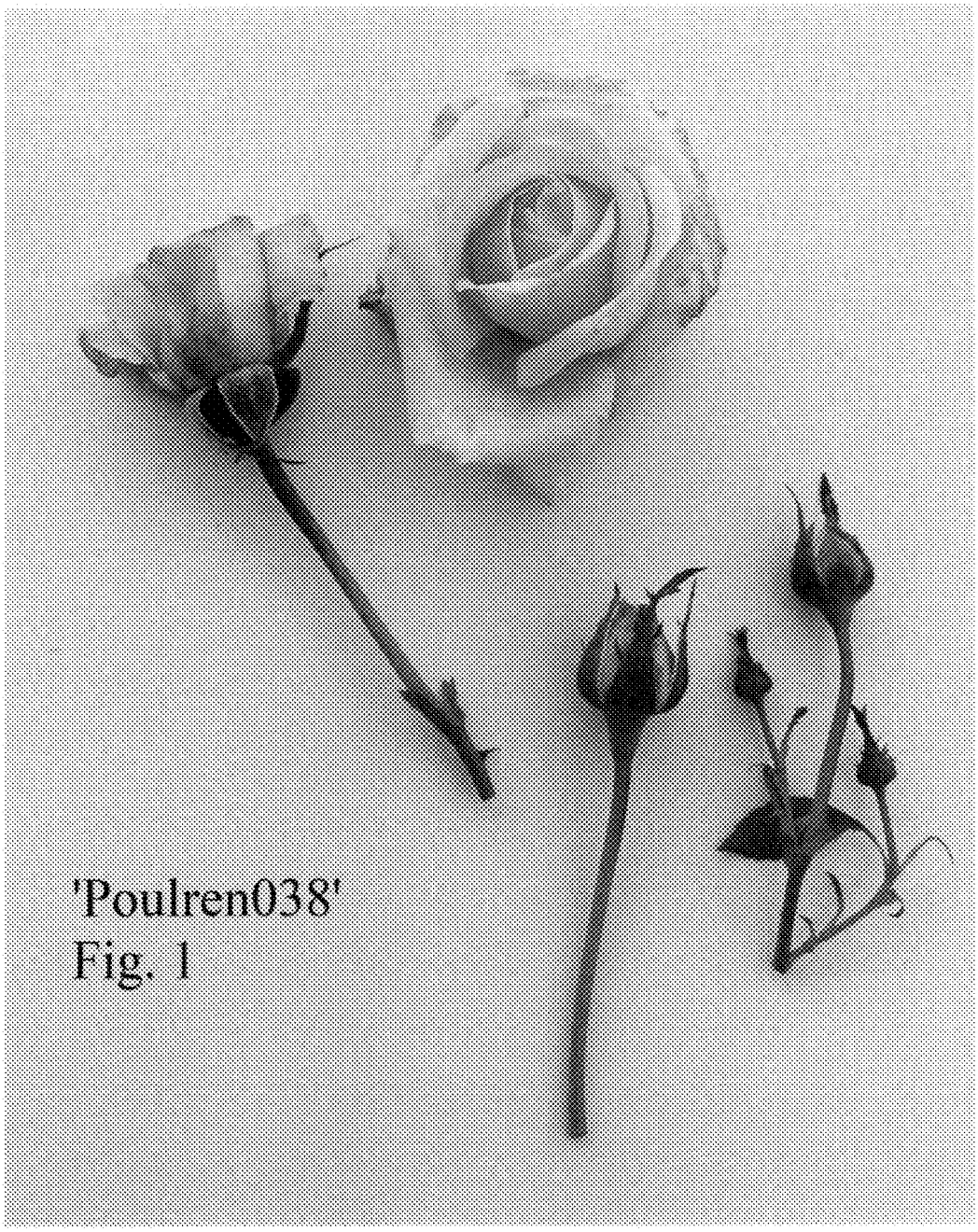
Figure 2:
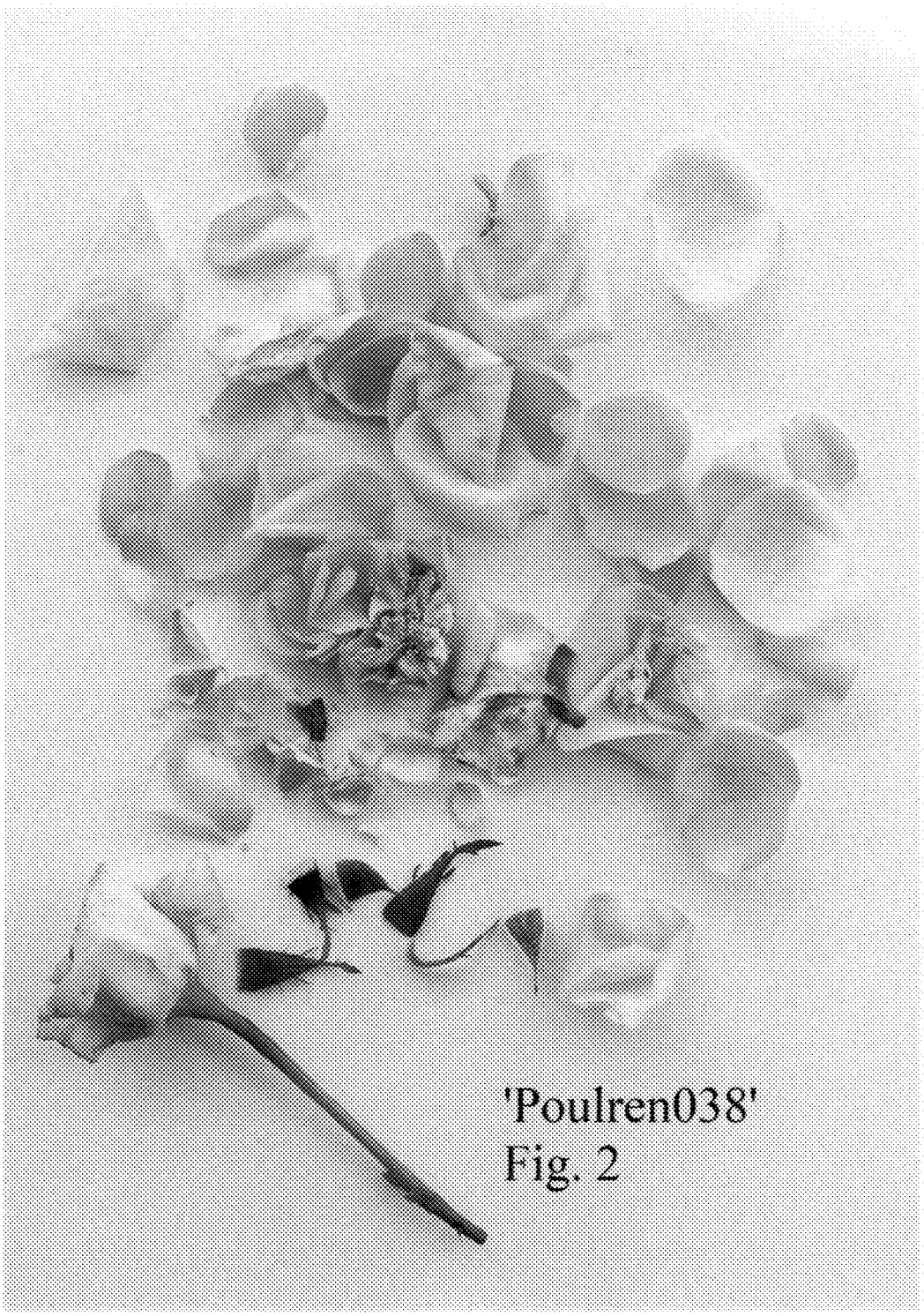

Specifically illustrated in FIG. 2 of the drawings are flower petals detached, sepals detached revealing reproductive flower parts.

Figure 3:
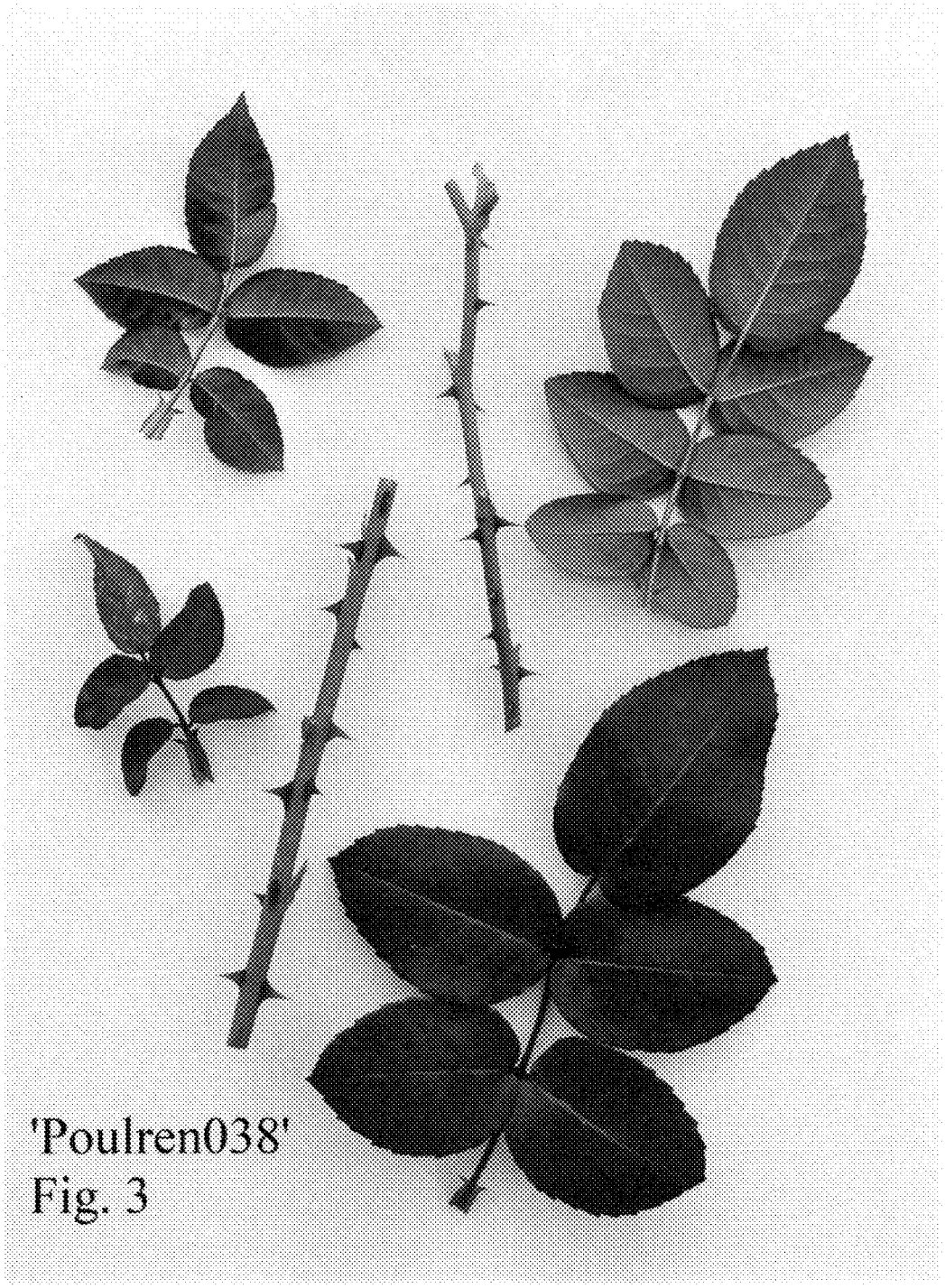

FIG. 3 illustrates the characteristics of the juvenile and mature leaves, bare stems and prickles.

Plants shown are 15 months of age.

DETAILED DESCRIPTION OF THE VARIETY

The following is a description of 'Poulren038', as observed in its growth in an outdoor nursery in Odense Denmark. Observed plants are 15 months of age, and were grown on their own roots in 30 cm pots. Color references are made using The Royal Horticultural Society (London, England) Colour Chart, 2001, except where common terms of color are used.

For a comparison, several physical characteristics of the rose variety 'Poulen011', U.S. Plant Pat. No. 15,167 are compared to 'Poulren038' in Chart 1.

CHART 1

| | 'Poulren038' | 'Poulen011' |
|---|---|---|
| Petal Count | 115 | 80 |
| Flower Diameter | 90 mm | 80 to 85 mm |
| General Tonality of Flower Color | Red Group 49A | Red Group 54D |

Flower and Flower Bud

Blooming habit: Continuous.

Flower bud:

*Size.*—Upon opening, 28 mm in length from base of receptacle to end of bud. Bud diameter is 17 mm.

*Bud form.*—Ovoid.

*Bud color.*—As sepals divide petals are Orange-Red Group 30D and Yellow Group 8C.

*Sepal inner surface.*—Color: Yellow-Green Group 146D. Surface: Lightly pubescent.

*Sepal outer surface.*—Color: Yellow-Green Group 144A with intonations of Greyed-Purple Group 183A. Texture: Smooth.

*Sepal shape.*—Apex: Cirrhose. Base: Flat at union with receptacle.

*Sepal margin.*—Margins have strong foliaceous appendages on three of the five sepals.

*Sepal size.*—40 mm long, 10 mm wide.

*Receptacle.*—Texture: Smooth. Size: 11 mm in height, 7 mm wide. Color: Yellow-Green Group 144A. Shape: Funnel.

*Pedicel.*—Surface: Smooth. Length: About 50 mm. Diameter: 3 to 4 mm. Color: Yellow-Green Group 144A with shades of Greyed-Red Group 183A. Strength: Strong.

*Peduncle.*—Length: 35 to 12 cm. Diameter: About 5 mm. Color: Yellow-Green Group 145A. Texture: Smooth, and with large prickles Greyed-Red Group 181A about 5 mm in length.

Flower bud development: Flower buds are borne in clusters of about 7 flower buds per stem.

Flower bloom:

*Fragrance.*—Strong, unripe banana and black tea.

*Duration.*—The blooms have a duration on the plant of approximately 18 days. Petals fall cleanly away from plant after flowers have fully matured.

*Size.*—Flower diameter is 90 mm when open. Flower depth is 45 mm.

*Flower shape.*—Quartered-rosette, very double, with many overlapping petals packed into quarter sections. Viewed from above the flower shape is irregularly round.

*Shape of flower, side view.*—The upper portion is flat convex. The lower portion is concave.

Petalage: Under normal conditions, flowers have about 115 petals.

General tonality of flower: Open flowers are Red Group 49A. Tonality does not change as the flower matures.

Petal color upon and after opening:

*Outer petals.*—Upper surface: The margins are Red Group 55C while the middle and basal zones are White Group N155C. Lower surface: At the basal and middle zone White Group N155C, with marginal intonations of Red Group 56D.

*Inner petals.*—Upper surface: Red Group 49A. At the medium size basal point of attachment Green-White Group 157B. Lower surface: Marginal zone Red Group 49B, middle zone Red Group 49C, basal zone medium size petal spot Green-White Group 157D.

Petals:

*Petal reflex.*—Moderate to strong.

*Margin.*—Entire and uniform. No undulations.

*Shape.*—Broad and elliptic. Apex shape: Rounded. Base shape: Acute.

*Size.*—About 50 mm (l)×45 mm (w).

*Texture.*—Smooth.

*Thickness.*—Average.

Petaloids:

*Size.*—18 mm (l) by 12 mm (w).

*Quantity.*—About 25.

*Shape.*—Elliptical with an acute base and rounded apices.

*Color.*—The upper surface is Red Group 49A with intonations of Green-Yellow Group 1D at the basal point of attachment. The lower surface is Red Group 49B.

Reproductive flower parts:

*Pollen.*—None observed.

*Anthers.*—Size: 1 mm in length. Color: Orange-White Group 159B. Quantity: 40 on average.

*Filaments.*—Color: Red Group 47B. Length: 10 mm.

*Pistils.*—Length: 10 mm. Quantity: 25 on average.

*Stigmas.*—Color: Yellow-Green Group 145D.

*Styles.*—Color: Yellow-Green Group 145D.

*Location of stigmas.*—Level with the anthers.

*Hips.*—None Observed.

Plant

Plant growth: Upright. Plants are 85 cm in height, and 55 cm wide.

Stems:

*Color of juvenile growth.*—Yellow-Green Group 144A.

*Color of mature growth.*—Yellow-Green Group 144A.

*Length.*—Canes are about 40 cm from the base of the plant to the flowering portion.

*Diameter.*—About 6 mm.

*Internodes.*—On mature canes about 50 to 65 mm between nodes.

*Surface texture.*—Young wood: Smooth. Older wood: Smooth.

Long prickles:

*Incidence.*—10 prickles per 10 cm of stem.

*Size.*—Average length of prickles on mature stems is 7 mm.

*Shape.*—Upper portion is linear. Lower portion is concave.

*Color.*—Juvenile prickles: Greyed-Purple Group 183B. Mature prickles: Greyed-Purple Group 183B.

Plant foliage:

*Compound leaf.*—165 mm (l)×125 (w).

*Quantity.*—2 leaves per 10 cm of stem on average.

*Leaf bearing angle to the stem.*—45 degrees.

*Color of juvenile foliage.*—Upper side: Yellow-Green Group 146A with strong intonations of Greyed-Purple Group 183B. Lower side: Yellow-Green Group 146B with strong intonations of Greyed-Purple Group 183B.

*Color of mature foliage.*—Upper side: Yellow-Green Group 147A. Lower side: Yellow-Green Group 147B.

Plant leaves and leaflets:

*Stipules.*—Size: 20 mm long, 3 mm wide. Quantity: 2 per compound leaf. Shape: Linear, slightly broad based with outward extending apices. Margins: Finely serrated. Color: Yellow-Green Group 144A.

*Petiole.*—Length: 35 mm. Diameter: 2 mm. Upper surface color: Yellow-Green Group 144A. Lower surface color: Yellow-Green Group 144A.

*Rachis.*—Length: 50 mm. Upper surface color: Yellow-Green Group 144A with intonations of Greyed-Purple Group 183C. Lower surface color: Yellow-Green Group 144A.

*Leaflet.*—Quantity: Normally 5 to 7 leaflets. Margins: Serrated. Size: Terminal leaflets are about 77 mm long, 36 mm wide. Shape: Generally elliptical. Base: Rounded. Apex: Acute. Texture: Smooth. Thickness: Average. Arrangement: Odd pinnate. Venation: Reticulate. Glossiness: Not glossy.

Disease resistance: Above average resistance to powdery mildew *Sphaerotheca pannosa* var. *rosae*, downy mildew *Peronospora sparsa*, rust *Phragmidium* spp., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant named 'Poulren038' substantially as described and illustrated herein.

* * * * *

'Poulren038'

'Poulren038'

'Poulren038'